United States Patent [19]

Geczy

[11] Patent Number: 5,744,165
[45] Date of Patent: Apr. 28, 1998

[54] NIMESULIDE SALT CYCLODEXTRIN INCLUSION COMPLEXES

[75] Inventor: Joseph Geczy, Bruxelles, Belgium

[73] Assignees: Europharmaceutical, S.A., Bruxelles, Belgium; Cyclolab Cyclodextrin Research and Development Laboratory, Ltd., Budapest, Hungary

[21] Appl. No.: 374,765

[22] PCT Filed: May 18, 1994

[86] PCT No.: PCT/HU94/00014

§ 371 Date: Mar. 21, 1995

§ 102(e) Date: Mar. 21, 1995

[87] PCT Pub. No.: WO94/28031

PCT Pub. Date: Dec. 8, 1994

[30] Foreign Application Priority Data

May 24, 1993 [HU] Hungary ............... P 93 01518

[51] Int. Cl.$^6$ ............... C08B 37/16; A61K 47/40; A61K 31/63
[52] U.S. Cl. ............... 424/499; 536/46; 536/103; 514/608; 514/646; 514/649; 514/651; 514/717
[58] Field of Search ............... 424/499; 536/46, 536/103; 514/608, 646, 649, 651, 717

[56] References Cited

U.S. PATENT DOCUMENTS 4,565,807  1/1986  Uekama et al. ............... 536/103

FOREIGN PATENT DOCUMENTS 0346006  12/1989  European Pat. Off. .
WO9117774  11/1991  WIPO .

OTHER PUBLICATIONS

M. Kurozumi, et al. "Inclusion Compounds of Non–Steroidal Antiinflammatory and Other Slightly Water Soluble Drugs with α– and β–Cyclodextrins in Powdered Form", Chem. Pharm. Bull. Vo. 23 (1975), pp. 3062–3068.

Primary Examiner—Nathan M. Nutter
Attorney, Agent, or Firm—Steinbegt, Raskin & Davidson, P.C.

[57] ABSTRACT

Inclusion complexes of nimesulide alkali and alkaline earth salts with cyclodextrins and cyclodextrin derivatives are disclosed. Compositions containing the inclusion complexes, processes for the preparation of the complexes as well as methods to use the same as pharmaceuticals are disclosed.

21 Claims, 3 Drawing Sheets

NIMESULIDE SALT CYCLODEXTRIN INCLUSION COMPLEXES

This application is filed under 35 USC 371 as a continuation PCT/HU94/00014 filed May 18, 1994.

FIELD OF THE INVENTION

The invention relates to highly soluble, physiologically acceptable inclusion complexes of nimesulide-salts with cyclodextrins, to the preparation thereof, to pharmaceutical compositions containing the same as well as methods for their use.

More particularly, the invention relates to inclusion complexes of nimesulide alkali and alkaline earth salts of general formula (I)

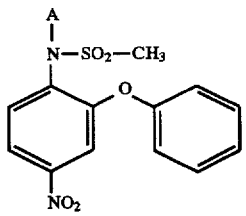

wherein A represents an alkali and/or alkaline earth ion; with cyclodextrins and cyclodextrin derivatives.

BACKGROUND OF THE INVENTION

Nimesulide [4-nitro-2-phenoxy-methane-sulfonailide] is known to be a potent non-steroidal antiinflammatory drug successfully used for the treatment of different painful inflammatory conditions and rheumatoid arthritis. It also possesses antipyretic activities (Belgian Patent No. 801812). Solutions of nimesulfide sodium salts were prepared from nimesulide with sodium carbonate in acetone and they were used without isolation as intermediates to prepare N-substituted nimesulide derivatives (Belgian Patent No. 801812). Probably due to the high pH value of their solutions, the nimesulide alkali and alkaline earth salts were not practical for use as pharmaceuticals. Recently, it has been confirmed that based on its mechanism of action in pain relief, nimesulide can also be considered to represent a new type of useful analgesic agent. Forsuch drugs a quick onset of action of the orally administered formulation is a very important factor.

Compared to other non-steroidal antiinflammatories, nimesulide has a favorable therapeutic index, minimal acute gastrointestinal toxicity and exhibits good general tolerability. It is chemically different from other drugs of its class because its functional acidic group is a sulfonanilide moiety.

Nimesulide is a very hydrophobic drug substance and is practically insoluble in water. Its aqueous solubility is about 0.01 mg/ml at room temperature. The very poor aqueous solubuility and wettability of the drug present problems for the preparation of pharmaceutical formulations with good release and non-variable bioavailability.

It is desirable to overcome the disadvantages connected with the very poor aqueous solubility and wettability in order to increase the aqueous solubility of nimesulide.

Nimesulide is a weak acid type compound; therefore its aqueous solubility in acidic medium, e.g., at the pH of the gastric juice, is particularly poor. Orally administered nimesulide is likely to be absorbed only in the lower part of the gastrointestinal tract. This probably explains the rather protracted onset of its biological effect, although other theories are possible to explain this observation.

Patent Applications PCT/IT91/00043 and DE 4116659 describe complexation of nimesulide with cyclodextrins, preferably with β-cyclodextrin in about a 1:1 molar ratio, and faster absorption and higher plasma levels of nimesulide were shown in animal tests when compared with administration of nimesulide per se.

For solid complex preparation, three different known methods are exemplified:

A. Precipitation from a water and organic solvent mixture by shaking overnight, the preferred solvent being methylene-chloride;

B. Freeze- or spray-drying from homogeneous aqueous ammonium hydroxide solution; and C. Stirring in aqueous suspension for several days at 60° C. and isolating the complex by evaporation under reduced pressure.

Method A is not acceptable for preparation of cyclodextrin (CD) compexes for pharmaceutical purposes. All organic solents form more or less stable complexes with cyclodextrins. Inclusion of methylene chloride by β-cyclodextrin is invevitable in this case; consequently the product might contain a considerable amount of toxic chlorinated solvent. The chlorinated solvent can not be removed completely even by heating in vacuo at elevated temperature for hours. The toxic chlorinated solvent will be released only upon dissolution, e.g., in the gastric juice.

Method C is the oldest known method for preparation of drug/cyclodextrin-complexes, but the long stirring time, with the concomitant degradation makes this process technically obsolete. Method B seems to be the best, however, it is difficult to completely remove ammonia during the freeze-drying procedure.

In the above-mentioned PCT and DE patent applications no data is given about the attainable solubility enhancement of nimesulide with β-cyclodextrin (βCD) or the dissolution behavior of the complexes prepared by the three different methods described.

It can be concluded that both pH alteration towards the alkaline region and complexation with βCD can enhance the solubility of nimesulide. βCD alone shows only a very moderate (about 5-fold) solubility enhancing effect which correlates to about 0.05 to about 0.06 mg/ml dissolved nimesulide in a saturated aqueous βCD solution. However, a significantly higher increase in solubility can be achieved only at pH beyond the physiologically acceptable values.

OBJECTS AND SUMMARY OF THE INVENTION

It is an object of the present invention to prepare highly soluble, physiologically acceptable inclusion complexes comprising nimesulide and cyclodextrins.

A further object of the invention is to provide efficient method(s) for producing said complexes having the said solubility or redissolving properties.

A still further object of the present invention is the new inclusion complexes of nimesulide alkali and alkaline earth salt of general formula (I)

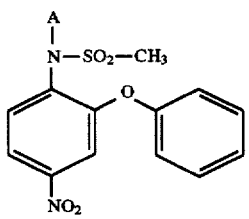

I.

wherein A is an alkali and/or alkaline earth ion; with cyclodextrins and cyclodextrin derivatives. These new products ensure a considerable 200–600 fold increase in solubility of nimesulide at physiological pH due to the synergistic effect of pH alteration and cyclodextrin complexation.

Preferred embodiments of the invention are inclusion complexes wherein the cyclodextrins and cyclodextrin derivatives are α, β and γ-cyclodextrins, and alkyl or hydroxyalkyl derivatives of cyclodextrin, preferably methyl β-cyclodextrins or hydroxypropyl-β-cyclodextrin.

Further preferred embodiments encompass inclusion complexes wherein the metal ion in the nimesulide salt is sodium or potassium. Alkaline earth salts, e.g., the calcium or magnesium salts might also be used.

Further embodiments of the invention are new pharmaceutical compositions containing as the active ingredient the highly soluble, physiologically acceptable inclusion complex of nimesulide alkali and alkaline earth salt and cyclodextrins or cyclodextrin derivatives as stated above.

A further embodiment of the invention provides a process for the preparation of inclusion complexes of nimesulide alkali and alkaline earth salts and cyclodextrins or cyclodextrin derivatives including the step of reacting nimesulide alkali and alkaline earth salts in the presence of water with cyclodextrins or cyclodextrin derivatives at about pH 7 to about 9.5, and preferably at about pH 7.5 to 8.5.

When carrying out this process, it is advantageous to use nimesulide alkali or alkaline earth salts formed in situ in the reaction mixture by adjusting the suspension of nimesulide in water to a pH value of about 7 to about 9.5, preferably about 7.5 to about 8.5, by the addition of alkali and alkaline earth hydroxides, alkali and alkaline earth carbonates, alkali and alkaline earth hydrogen carbonates, alkali and alkaline earth phosphates. Preferred pH-adjusting compounds include sodium hydroxide, disodium phosphate and/or sodium hydrogen carbonate. Buffers may also be used to adjust the desired pH-values.

After formation of the complex, water may be removed by freeze-drying, spray-drying, low temperature vacuum evaporation, vacuum drying or other methods known in the art. Aqueous solutions of the complexes or solutions containing the complex formed in situ from the ingredients nimesulide salt and cyclodextrins or cyclodextrin derivatives are also encompassed by the present invention.

DETAILED DESCRIPTION OF THE INVENTION

The inclusion complexes according to the present invention were prepared with α, β and γ-cyclodextrin or with highly soluble hydroxy alkylated and methylated β-cyclodextrin derivatives. Preferred cyclodextrins include randomly methylated β-cyclodextrin, DIMEB or TRIMEB.

The inclusion complexes according to the invention can easily be redissolved in distilled water or physiological saline to obtain clear or slightly opalescent solutions at physiological pH values of 200–600 times higher dissolved nimesulide concentration than would be obtained from aqueous solutions of nimesulide alone.

Pharmaceutical compositions which include as the active ingredient the inclusion complexes of nimesulide alkali and alkaline earth salts and cyclodextrins or cyclodextrin derivatives may be prepared by any methods known in the pharmaceutical art.

Pharmaceutical compositions of particular importance are those containing as active ingredient the inclusion complex of nimesulide sodium salt and β-cyclodextrin. The compositions may contain other pharmaceutically acceptable ingredients such as used for formulation by the pharmaceutical industry.

The complexes and compositions according to the present invention can be used in pharmaceutical formulations administered by oral, parenteral, rectal or topical route. The aqueous solutions of the complexes can also be used in sprays.

A further embodiment of the invention includes methods of treating patients in need of antiinflammatory and/or analgetic treatment. The methods include administering to the patient an effective amount of an inclusion complex of cyclodextrins or cyclodextrin derivatives formed with nimesulide alkali and alkaline earth salt.

While applicant is not bound by theory, most probably the complex—after dissolution in the gastrointestinal tract—is subject to an equilibrium whereby molecularly dispersed nimesulide is formed in the gastric juices accelerating and improving absorbance and action of the drug.

The invention is illustrated by the following Examples without restricting the scope to their contents.

EXAMPLES

EXAMPLES OF CHEMICAL SYNTHESIS AND SOLUBILITY

Example 1

Excess amounts of nimesulide were stirred at 30° C. in 5 ml samples of distilled water, pH 7.6, 8.0 and 9.6 alkali phosphate buffer solutions containing 0.0, 0.5, 1 and 1.8% (w/v) of β-cyclodextrin. After 18 hours of equilibration the suspensions were filtered across a 0.45 μm membrane filter. The dissolved nimesulide contents of the filtrates were analyzed by spectrophotometry after appropriate dilution with 0.05N hydrochloric acid in 50% (v/v) ethanol. Absorbance at √ max 300±3 nm was used for quantitative calculation.

Table 1 summarizes the obtained results, the final pH values of the filtered solutions are also indicated.

TABLE 1

| βCD % | Dist. Water | Dissolved Nimesulide mg/ml | | | Final pH of solutions | | |
|---|---|---|---|---|---|---|---|
| | | pH 7.6 | pH 8.0 | pH 9.6 | pH 7.6 | pH 8.0 | pH 9.6 |
| 0 | 0.010 | 0.034 | 0.07 | 0.28 | 7.40 | 7.70 | 8.30 |
| 0.5 | 0.024 | 0.170 | 0.26 | 0.80 | — | — | — |
| 1.0 | 0.035 | 0.330 | 0.42 | 1.27 | 7.30 | 7.46 | 8.09 |
| 1.8 | 0.054 | 0.570 | 0.85 | 1.79 | 7.24 | 7.45 | 7.92 |

Figure 1:
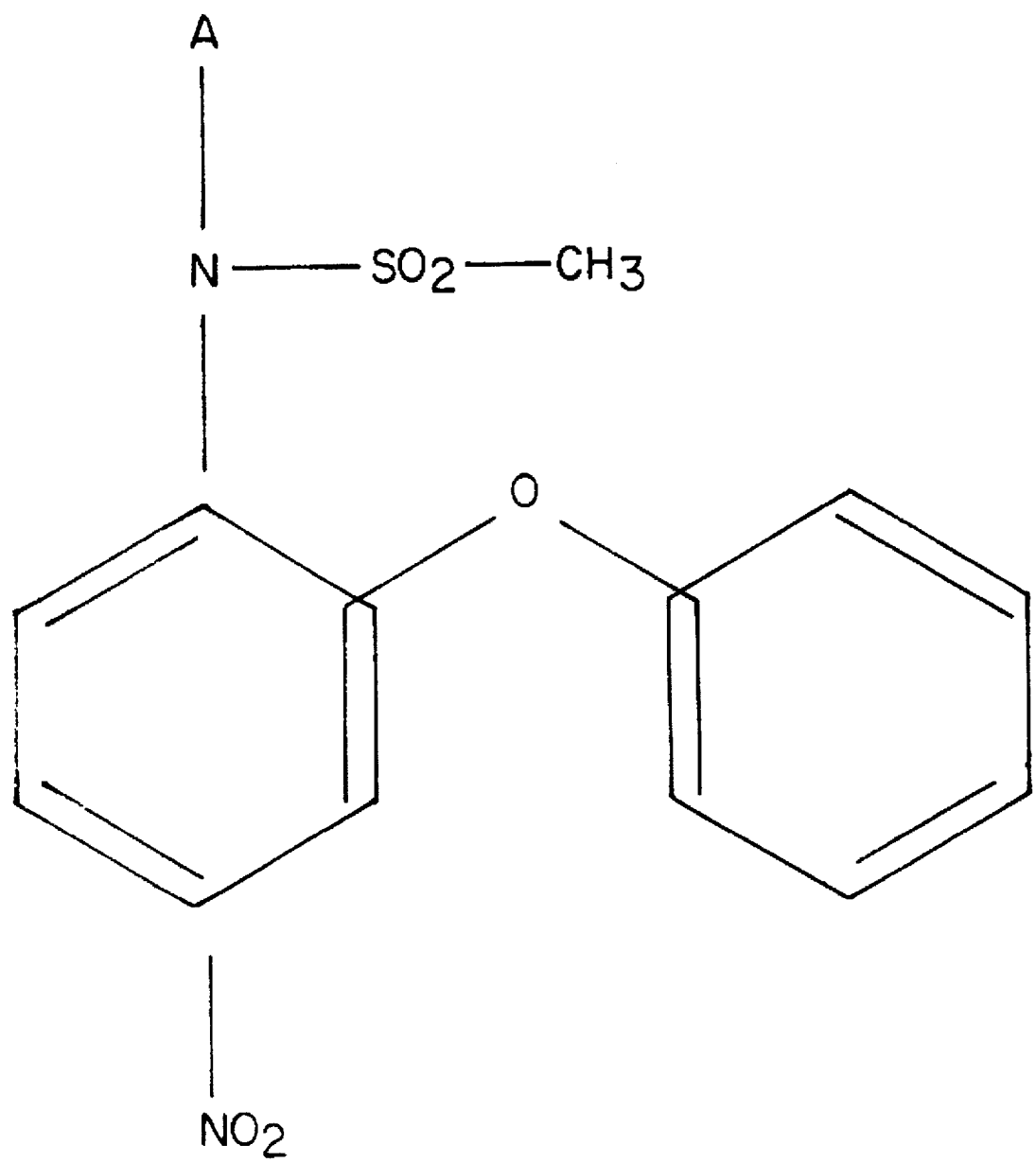
FIG. 1 is a representation of the general chemical structure of the inclusion complexes of nimesulide alkali and alkaline earth salts of the present invention.
Figure 2:
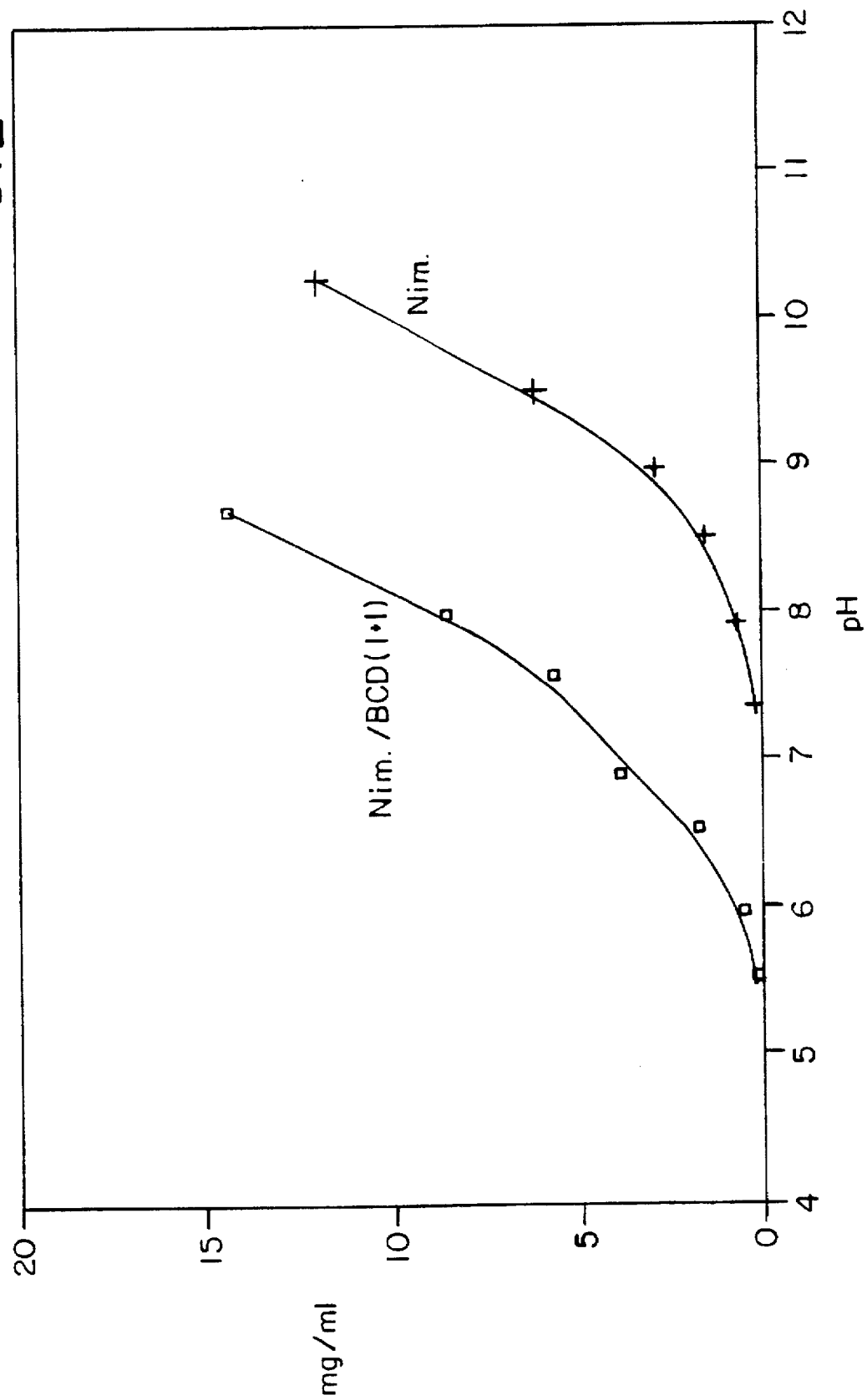
FIG. 2 is a graphical representation demonstrating the solubility of nimesulide in the presence and absence of β-cyclodextrin as a function of pH.

Nimesulide-Na solutions alone and in the presence of equimolar βCD were titrated with 0.1N $H_3PO_4$. At different pH values, the opalescence of the solution became stronger (correlating to drug precipitation). Samples are analyzed for dissolved nimesulide content by UV spectrophotometry. FIG. 2 shows the decrease of nimesulide solubility in the presence and absence of βCD as a function of pH. Dissolved nimesulide in mg/ml is shown against pH values. At around pH 8 almost all nimesulide remains dissolved in presence of βCD while almost all of the whole drug precipitates from the control solution. (About 10 mg/ml dissolved nimesulide as compared with less than 1 mg/ml.) The $pK_a$ of nimesulide is shifted to a lower value by CD-complexation.

Example 2

95 grams of β-cyclodextrin (0.076 moles, water content 10%) are suspended in 1200 ml of distilled water with vigorous stirring and 12 grams (0.038 moles) of nimesulide dissolved in 80 ml of 0.5N aqueous sodium hydroxide solution are added. When a homogenous solution is obtained, the pH of the solution is adjusted with 0.5M $H_3PO_4$ to pH 8.2–8.6 and the yellow solution is freeze-dried to isolate the solid complex. 98 grams nimesulide sodium salt/βCD complex of 1:2 molar ratio (a bright yellow fine powder) is obtained. The resultant nimesulide content is 11.8±0.1% measured by UV-spectrophotometry.

Solubility properties of the complex are such that 100 mg of the product can be dissolved in 3 ml of distilled water resulting in a yellow solution with approximately 4 mg/ml nimesulide content, the solution having a pH vlaue of 7.6±0.1.

The DSC curve of the complex is identical with that of the complex obtained according to Example 3 below. Disappearance of the endothermic peak at 240°–241° C. points to the absence of free nimesulide in the inclusion complex of 1:1 nimesulide sodium-βCD (molar ratio).

Example 3

33.2 grams of β-cyclodextrin (0.025 moles, water content 13.7%) are suspended in 550 ml of distilled water. 8.25 grams of nimesulide (0.025 moles) are dissolved in 60 ml of a 0.5N aqueous sodium hydroxide solution and added to the suspension of β-cyclodextrin under vigorous stirring, resulting in a clear dark yellow solution. The pH of the solution is adjusted with 0.5N $H_3PO_4$ to a pH of about 8.5–8.7. The solution is freeze-dried to obtain the solid complex.

41 grams of nimesulide-sodium salt/βCD complex of 1:1 molar ratio are obtained as a yellow fine powder. The resultant nimesulide content is 20.0±0.2% measured by UV-spectrophotometry. Solubility properties are such that 100 mg of the complex can be dissolved in 6 ml of distilled water, resulting in a slightly opalescent solution with approximately 3.5 mg/ml nimesulide content. The solution has a pH value of 8.3±0.1.

Differential scanning calorimetry (DSC) curves show characteristic differences between the physical mixture and the lyophilized complex. The sharp endothermic heat flow peak characteristic for the melting of nimesulide appears at 240°–241° C. on the DSC curve of the physical mixture, followed by a strong exothermic DSC peak characteristic for thermal decomposition of βCD. The DSC pattern of the inclusion complex does not exhibit any endothermic heat flow in the melting range indicating the formation of an inclusion complex between the salt and β-cyclodextrin. Only a strong exothermic DSC peak characteristic for thermal decomposition of βCD can be observed.

Figure 3A:
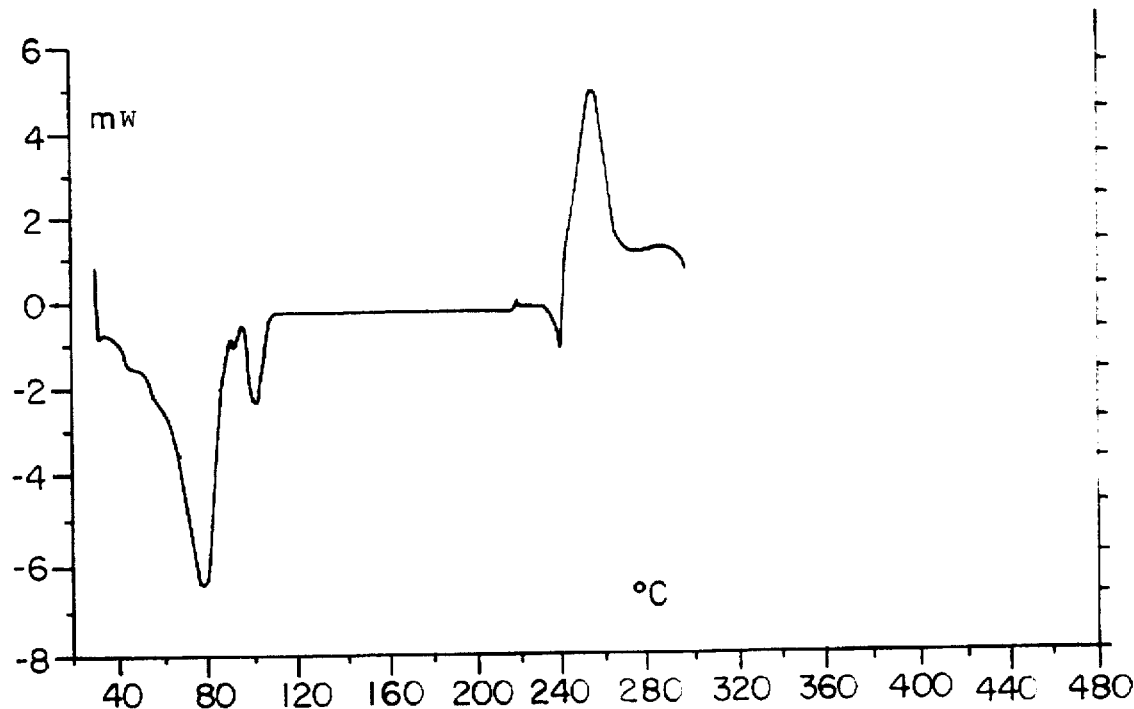
FIG. 3(A) is a graphical representation of the DSC curves of the nimesulide-sodium:β-cyclodextrin 1:2 physical mixture.
Figure 3B:
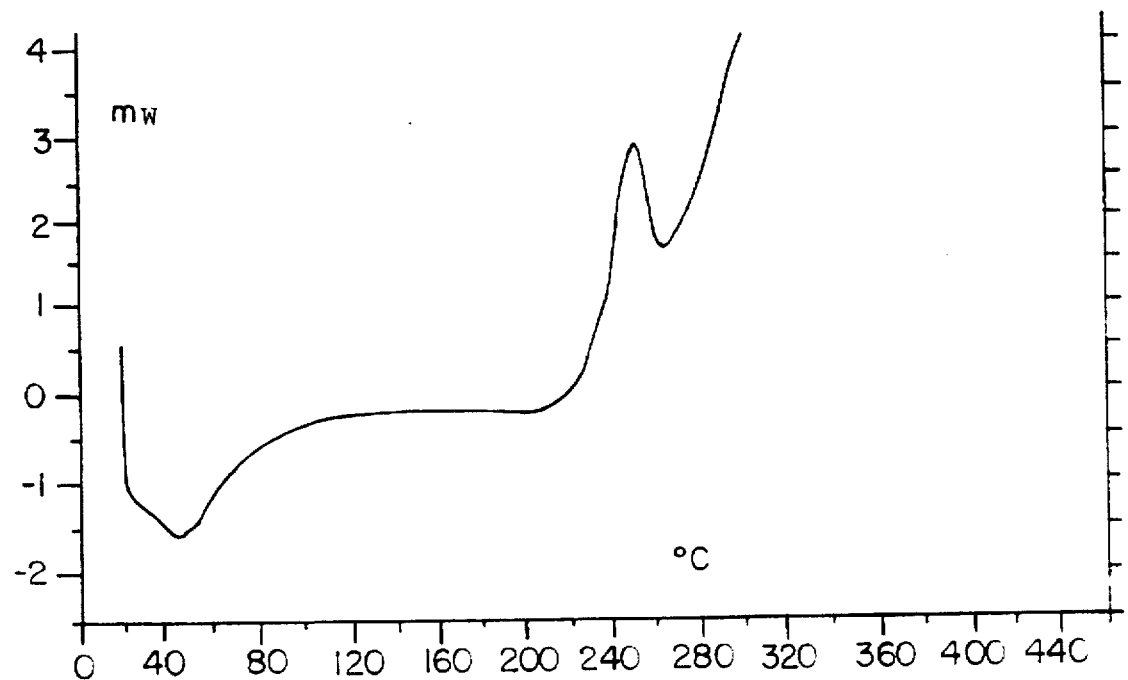
FIG. 3(B) is a graphical representation of the DSC curve of the nimesulide-sodium β-cyclodextrin complex prepared according to Example 3.

FIG. 3 shows the DSC curves of the nimesulide-sodium: βCD=1:2 physical mixture (A) and the nimesulide-sodium/ βCD complex (B) prepared according to Example 3:Heat flow (mW) is represented as a function of temperature (°C.) [DuPont 1090 Thermal Nalyzer, scanning rate 5° C./min. argon atmopshere].

A nimesulide-potassium salt/βCD complex may be prepared according to the same method, using KOH instead of NaOH.

Nimesulide-calcium and magnesium salt/CD complexes can be prepared in a similar manner.

Example 4

30.2 grams of β-cyclodextrin (0.024 mols, water content 10%) and 3.75 grams of nimesulide (0.012 moles) are suspended in 25 ml of a 0.5N aqueous sodium hydroxide solution. The thin suspension is stirred by an Ultra Turrax high speed dispersing apparatus with r.p.m. approx. $10^3$ for five minutes. The pH of the alkaline non-transparent solution is adjusted below pH 9.0 with 1N aqueous hydrochloric acid. The solid complex is isolated by drying at 40° C. under vacuo, and the dry complex is powdered.

34 grams of nimesulide-sodium salt-βCD complex (1:2) are obtained as a yellow fine powder. Nimesulide content: 11±0.1% measured by UV-spectrophotometry.

Solubility: 100 mg of the complex dissolved in 3 ml of distilled water resulted in an opalescent solution with approximately 3 mg/ml dissolved nimesulide content. The solution exhibited a pH value of 7.3±0.1.

Example 5

40 grams of randomly methylated β-cyclodextrin (RAMEB 0.034 moles, average degree of substituion per glucose unit is 1.8) are dissolved in 300 ml of distilled waater. 5.4 grams of nimesulide (0.017 moles) dissolved in 17 ml of 1N aqueous sodium hydroxide are added whereupon the pH of the solution is adjusted with 0.5N $H_3PO_4$ to pH 7.7±0.1. The yellow solution is freeze-dried to isolate the solid complex.

45 grams of nimesulide-sodium salt-randomly methylated-β-cyclodextrin (RAMEB) complex of 1:2 molar ratio are obtained in the form of a fine yellow powder having a nimesulide content of 11.1±0.1% measured by UV-photometry.

The solubility is such that 100 mg of the complex dissolved in 2 ml of distilled water result in a yellow solution (pH 7.3±0.1) with approproximately 6 mg/ml nimesulide content.

Example 6

2.6 grams of gamma-CD (0.002 moles) are dissolved in 20 ml of distilled water and 0.308 grams (0.001 moles) of nimesulide dissolved in 5 ml of 0.2N aqueous sodium hydroxide are added, whereupon the pH of the solution is adjusted to pH 7.4–7.5, and the yellow solution is freeze-dried. 2.9 grams of nimesulide sodium salt/gamma-CD complex of 1:2 molar ratio are isolated in the form of a very fine yellow powder. Then nimesulide content exhibited is 10.5±0.2% measured by UV-photometry. 100 mg of the complex was dissolved in 2 ml of distilled water give a clear yellow solution with approximately 5 mg/ml nimesulide content (pH=7.3±0.1).

Example 7

13 grams of hydroxypropyllated βCD (0.01 mole, average degree of substitution per glucose unit is 2.7) are dissolved in 150 ml of distilled water and 1.54 grams of nimesulide (0.005M) and 5 ml of 1N sodium hydroxide are added while stirring. A dark clear yellow solution is obtained. The pH of the solution is adjusted to 7.5±0.1 with 0.2N phosphoric acid, and the solution is freeze-dried.

14 grams of nimesulide sodium/HPβCD complex of 1:2 molar ratio are obtained in the form of a very fine yellow powder.

The nimesulide content exhibited was 10.6±0.2% measured by UV photometry. 100 mg of this complex dissolved in 2 ml of distilled water resulting in a clear yellow solution with about 5 mg/ml dissolved nimesulide content (pH of the solution=7.4±0.1).

Example 8

The dissolution of nimesulide-Na/βCD complex prepared according to Example 2 was compared to nimesulide-Na and nimesulide-Na/βCD complex prepared in situ from the corresponding 1:2 molar physical mixture of the components. Simulated gastric juice was used as a medium. 100 mg of nimesulide, an equivalent amount of the isolated complex and the physical mixture of the ingredients were stirred in 20 ml of pH 1.4 aqueous HCl solution. Samples were taken at 2, 15 and 60 minutes. On filtration, the nimesulide content was measured by UV photometry. Average results of three experiments are summarized in Table 2.

TABLE 2

| | Concentration of Dissolved Nimesulide (µg/ml) | | |
|---|---|---|---|
| Time (min) | Nim.-Na | Nim-Na/βCD isolated complex | Nim.-Na/βCD in situ complex |
| 2 | 5.4 ± 0.7 | 35.4 ± 1.4 | 33.3 ± 2.2 |
| 15 | 4.0 ± 0.1 | 36.1 ± 0.25 | 33.3 ± 0.3 |
| 60 | 4.4 ± 0.5 | 34.6 ± 1.5 | 35.1 ± 0.2 |

The measurable nimesulide concentration both for the isolated complex and the in situ formed complex are approximately five times higher than in the case of nimesulide-Na substance. This higher concentration is maintained even after 60 minutes. The results indicate that in situ complex formation from the physical mixture took place under the conditions employed.

Example 9

A comparative solubility test was carried out using nimesullide-Na/βCD complex tablets (100 mg), Mesulid commercial tablets (batch No. 891 1026/SCAD 91/11. 100 mg) and nimesulide-Na salt substance (prepared by lyophilization from a solution of 1:1 molar ratio nimesulide and sodium hydroxide, using an equivalent amount to 100 mg of nimsulide).

Powdered tablets of each sample were suspended in 20 ml of pH 1.4 aqueous HCl solutions and stirred at ambient temperature. Samples were taken after 2, 60 and 90 minutes. On filtration the nimesulide concentration of the filtrates was evaluated by UV-spectrophotometry after dilution with 96% ethanol. Absorbance at MAX=299±1 nm was used for quantitative calculation taken $E_{1cm}$ 299±1 nm=257 for nimesulide. Results are summarized in Table 3.

TABLE 3

| NIMESULIDE CONCENTRATIONS AS A FUNCTION OF TIME AT pH = 1.4 | | | |
|---|---|---|---|
| | Nimesulide conc. (µg/ml) | | |
| | 2 min. | 60 min. | 90 min. |
| Nim.-Na/βCD tbl. | 35 | 43 | 37 |
| Mesulid tbl. | 10 | 14 | 11 |
| Nim.-Na salt | 7 | 10 | 6 |

Table 3 shows that considerable solubility differences are found in favor of the complex tablets. It is obvious that the solubility of an acid type drug might be lower in a pH 1.4 solution than in water. The alkali salts of the drug are freely soluble in water. Their in vivo absorption, however, after oral administration is delayed due to the precipitation of the acid-form under the pH of the stomach.

βCD complexation enhances solubility of nimesulide also under acidic pH conditions. Based on the above in vitro findings, an improved absorption of nimesulide-salt complexes is understood after oral administration because the solubiity under acidic pH is a necessary precondition, e.g., for faster onset of action.

Example 10

2.3 grams of βCD (0.002 moles), water content 14%, and 0.31 grams of nimesulide (0.001 moles) are suspended in 100 ml of distilled water. 2 ml of 0.5N aqueous potassium hydroxide are added while stirring. The pH of the dark yellow solution obtained is adjusted below 9 using 0.5N hydrochloric acid. 2.8 grams of nimesulide-K/βCD complex (1:2) are isolated by freeze-drying. Analysis with UV spectrophotometry revealed a nimesulide content of 10.8±0.2%.

The complex exhibited a solubility of 100 mg of the above complex are dissolved in 3 ml of distilled water. A clear or slightly opalescent solution with ≈3 mg/ml dissolved nimesulide results, pH 7.8±0.1.

EXAMPLES OF PHARMACEUTICAL COMPOSITIONS

Example 11

Composition of tablets with 50 mg and 100 mg of nimesulide content:

| | | |
|---|---|---|
| Nimesulide-sodium salt/βCD complex (Example 3) | 250 mg | 500 mg |
| Calcium phosphate | 60 mg | 85 mg |
| Lactose | 35 mg | 45 mg |
| Magnesium-stearate | 5 mg | 5 mg |
| Total | 350 mg | 540 mg |

The complex is homnogenized with the additives and directly pressed into tablets.

Example 12

Composition of granule sachet formulation wtih 50 mg and 100 mg of nimesulide content of each:

| | | |
|---|---|---|
| Nimesulide-sodium salt/βCD | 450 mg | 900 mg |
| Sorbite | 2500 mg | 4000 mg |
| Lemon flavor | 15 mg | 30 mg |
| Saccharine | 5 mg | 5 mg |
| Total | 2970 mg | 4935 mg |

The complex is homogenized with sorbite and additives and filled into sachets.

Example 13

Composition of oral liquid formulation with 50 mg/10 ml nimesulide content.

| | |
|---|---|
| Nimesulide-K/βCD complex (Example 3) | 2.500 g |
| Hydroxypropyl cellulose | 0.200 g |
| Potassium sorbate | 0.150 g |
| Fructose | 5.0 g |
| Saccharine sodium | qu. sat. |
| Demineralized water | ad 100.0 ml |

The viscosity enhancer is dissolved in about 80 ml of warm demineralized water and the complex added and dissolved. Other additives are added to obtain a homogeneous solution. Each spoon (~10 ml) contains 50 mg of nimesulide.

Exmple 14

Composition of ointment with 10 mg/1 g nimesulide content:

| | |
|---|---|
| Complex of Example 5 | 9 g |
| Hydrophilic Ointment | 91 g |
| Total | 100 g |

The hydrophilic ointment base is melted at 50°–60° C. and the nimesulide-salt complex is added under stirring to obtain a homogenously dispersed system. Under continuous stirring the ointment is cooled to room temperature and put into containers of 100 g.

Example 15

Composition of a parenteral formulation containing 5 mg/ml of nimesulide sodium salt-gamma-CD complex:

| | |
|---|---|
| Complex of Example 6 | 500 mg |
| Sodium chloride | 81 mg |
| Distilled water for injections | ad 10 ml |

Proper volumes of the complex solution are filled into containers with 50 mg nimesulide content each and lyophlized Before use, the lyophilized powder is dissolved with distilled water.

Exmple 16

Composition of suppository containing 50 mg of nimesulide:

| | |
|---|---|
| Complex of Example 3 | 250 mg |
| Polyethylene glycol-suppository base | 1250 mg |
| Total | 1500 mg |

The complex is homogenized with the melted suppository base and formulated to give suppositories.

Example 17

Hard gelatine capsules used for in situ complexes:

| | | |
|---|---|---|
| Nimesulide-Na | 53.5 mg | 107 mg |
| βCD | 214 mg | 428 mg |
| Mg stearate | 2.5 mg | 5 mg |
| Total | 270 mg | 540 mg |

The complex is formed when dissolving the capsule in acidic medium or after administration in the gastrointestinal tract.

Other useful embodiments will become apparent to those skilled in the art, and are meant to be encompassed within the scope of this invention.

What is claimed is:

1. An inclusion complex comprising 1) a nimesulide salt selected from an alkali salt and an alkaline earth salt, and 2) a cyclodextrin or a cyclodextrin derivative.

2. The inclusion complex of claim 1, wherein said nimesulide salt comprises the structure:

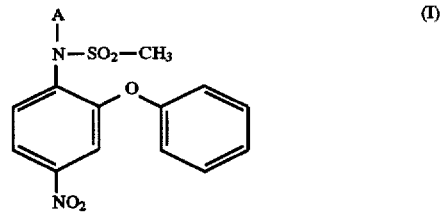

wherein A is an alkali or alkaline earth ion.

3. The inclusion complex of claim 2, wherein said nimesulide salt comprises a member of the group consisting of sodium, potassium, calcium and magnesium.

4. The inclusion complex of claim 1, wherein said nimesulide salt and said cyclodextrin or cyclodextrin derivative are present in a molar ratio of from about 1:1 to about 1:2.

5. The inclusion complex of claim 1, wherein said cyclodextrin is selected from the group consisting of α cyclodextrins, β cyclodextrins, γ cyclodextrins and mixtures thereof.

6. The inclusion complex of claim 1, wherein said cyclodextrin derivative is selected from the group consisting of alkyl cyclodextrins, hydroxyalkyl cyclodextrins and mixtures thereof.

7. The inclusion complex of claim 6, wherein said cyclodextrin derivative is selected from the group consisting of methyl β-cyclodextrins, hydroxypropyl-β-cyclodextrins and mixtures thereof.

8. The inclusion complex of claim 3, wherein said nimesulide salt is nimesulide sodium salt.

9. A process for the preparation of an inclusion complex of 1) a nimesulide alkali salt or a nimesulide alkaline earth salt, and 2) a cyclodextrin or a cyclodextrin derivative, which process comprises:

reacting a nimesulide alkali salt or a nimesulide alkaline earth salt with a cyclodextrin or cyclodextrin derivative in the presence of water at a pH of from about 7 to about 9.5.

10. The process of claim 9, wherein said pH is from about 7.5 to about 8.5.

11. The process of claim 9, further comprising forming the nimesulide alkali salt or nimesulide alkaline earth salt in situ in a reaction mixture containing nimesulide and the cyclodextrin or cyclodextrin derivative by adjusting the pH of said reaction mixture containing said nimesulide to from about 7 to about 9.5 by addition of a member of the group consisting of alkali hydroxides, alkaline earth hydroxides, alkali carbonates, alkaline earth carbonates, hydrogen carbonates, phosphates and mixtures thereof.

12. The process of claim 11, wherein said pH is adjusted to from about 7.5 to about 8.5.

13. The process of claim 11, wherein said alkali hydroxide is sodium hydroxide.

14. The process of claim 11, wherein said alkaline earth carbonate is sodium hydrogen carbonate.

15. The process of claim 11, wherein said phosphate is disodium phosphate.

16. The process of claim 9, further comprising removing said water after formation of said inclusion complex by drying said complex.

17. The method of claim 16, wherein said drying is carried out by freeze drying, spray drying, low temperature vacuum evaporation or vacuum drying.

18. A pharmaceutical composition comprising the inclusion complex of claim 1.

19. The pharmaceutical composition of claim 18, wherein said inclusion complex comprises the nimesulide sodium salt and β cyclodextrin.

20. A method of treating a patient in need of antiinflammatory treatment, analgesic treatment, or both antiinflammatory and analgesic treatment comprising administering to the patient an antiinflammatory, analgesic or antiinflammatory and analgesic effective amount of an inclusion complex comprising:

1) a nimesulide salt selected from an alkali salt and an alkaline earth salt, and 2) a cyclodextrin or a cyclodextrin derivative to the patient.

21. The method of claim 20, wherein said inclusion complex comprises the nimesulide sodium salt and β cyclodextrin.

* * * * *